(12) United States Patent
Ran et al.

(10) Patent No.: US 10,301,601 B2
(45) Date of Patent: May 28, 2019

(54) METHOD FOR TERMINAL INACTIVATION OF PATHOGENIC MICROORGANISMS

(71) Applicant: SICHUAN YUANDASHUYANG PHAMACEUTICAL CO. LTD, Chengdu (Sichuan Province) (CN)

(72) Inventors: Shuguang Ran, Chengdu (CN); Qiang Wang, Chengdu (CN); Dexi Jiang, Chengdu (CN)

(73) Assignee: Sichuan Yuandashuyang Phamaceutical Co., Ltd, Chengdu (CN)

( * ) Notice: Subject to any disclaimer, the term of this patent is extended or adjusted under 35 U.S.C. 154(b) by 109 days.

(21) Appl. No.: 14/580,200

(22) Filed: Dec. 22, 2014

(65) Prior Publication Data

US 2016/0053233 A1    Feb. 25, 2016

Related U.S. Application Data

(63) Continuation-in-part of application No. PCT/CN2013/078283, filed on Jun. 28, 2013.

(30) Foreign Application Priority Data

Jun. 28, 2012   (CN) .......................... 2012 1 0219659

(51) Int. Cl.
*C12N 7/00*      (2006.01)
*A61L 2/00*      (2006.01)

(52) U.S. Cl.
CPC .............. *C12N 7/00* (2013.01); *A61L 2/0023* (2013.01); *C12N 2750/14361* (2013.01)

(58) Field of Classification Search
None
See application file for complete search history.

(56) References Cited

U.S. PATENT DOCUMENTS 4,495,278 A * 1/1985 Thomas ................ A61K 39/12
                                                      435/5
6,485,725 B1 * 11/2002 Hirao .................. C07K 16/065
                                                      424/176.1

OTHER PUBLICATIONS

Bakaltcheva et al. Thrombosis Research 2007, vol. 120, pp. 105-116.*
Murrell et al., J gen Microbiol. 1966 vol. 43, pp. 411-425.*
Schneider, et al., Thrombosis and Haemostasis 2004: 92/4 (Oct) pp. 672-895.*
Masuda., J Phys Chem vol. 91, pp. 6543-6547, 1987.*

* cited by examiner

*Primary Examiner* — Shanon A. Foley
*Assistant Examiner* — Myron G Hill
(74) *Attorney, Agent, or Firm* — Wayne & Ken, LLC

(57) ABSTRACT

The present invention discloses a method for terminal inactivation of pathogenic microorganisms, comprising the following steps of: a. vacuum freeze-drying a bio-product packaged in a container, feeding in a gas and sealing to obtain the end product and, b. performing inactivation by dry-heating. The method provided by the present invention can effectively inactivate non-lipid enveloped viruses, with excellent inactivation effects and short inactivation time particularly to parvoviruses, and thus overcome the deficiencies of the conventional terminal dry-heating inactivation methods.

7 Claims, 2 Drawing Sheets

METHOD FOR TERMINAL INACTIVATION OF PATHOGENIC MICROORGANISMS

CROSS-REFERENCE TO RELATED APPLICATIONS

This application is a continuation-in-part of International Patent Application No. PCT/CN2013/078283 with an international filing date of Jun. 28, 2013, designating the United States, now pending, and further claims priority benefits to Chinese Patent Application No. 201210219659.7 filed Jun. 28, 2012. The contents of all of the aforementioned applications, including any intervening amendments thereto, are incorporated herein by reference.

TECHNICAL FIELD

The present invention relates to a method for inactivating pathogenic microorganisms, and in particular to a method for terminal inactivation of pathogenic microorganisms.

BACKGROUND OF THE PRESENT INVENTION

Bio-products are products produced by conventional technologies or modern biotechnologies from microorganisms, cells, animal or human tissues and body fluids, etc., as raw materials for prophylaxis, therapy and diagnosis of human diseases. Blood products, belonging to bio-products, mainly refer to bioactive preparations prepared by biological processes or by separation and purification technologies from healthy human blood as raw material, including human serum albumin, albumin prepared from human placenta, human immunoglobulin for intravenous injection, human immunoglobulin for intramuscular injection, histamine human immunoglobulin, specific immunoglobulin, hepatitis B, hydrophobia, tetanus immunoglobulin, human coagulation factor VIII, human prothrombin complex concentrate, human fibrinogen, anti-lymphocyte immunoglobulin, etc. The blood products, for purposes of treatment and passive immunization, play an irreplaceable role in providing emergency medical services, rescuing the wounded in wars, and preventing and treating some specific diseases.

As the blood products are prepared from human plasma, usually by mixing a plurality of portions of plasma and then processing by a certain separation and purification technology, theoretically, blood-borne diseases may be spread through the blood products. At present, the common viruses carried and spread by blood preparations mainly include HBV, HCV, HIV and HTLV-1, CMV, EBV, HAV, parvoviruses, etc.

To improve the safety of the blood products, according to requirements of the relevant guidance and principle, the production process of blood products must have the ability to remove/inactivate some viruses, and there should be specific virus removal/inactivation approaches available during the production. The virus inactivation approaches for the blood products are classified into physical inactivation and chemical inactivation. The physical inactivation typically includes pasteurization, dry-heating, γ-ray irradiation and short-wave ultraviolet irradiation. The chemical inactivation typically includes organic solvent/decontaminant (S/D) treatment, low pH incubation, caprylate inactivation and photochemical treatment. The chemical inactivation has good effect on lipid enveloped viruses only but very little on non-lipid enveloped viruses; furthermore, one or more biochemical reagents need to be added in the chemical inactivation, resulting in uncertain long-term safety. (Song Qingshuang, et al., *Progress of Virus Inactivation and Removal Process for Blood Products*, Letters in Biotechnology, 2012, No. 04). The majority of bio-products are manufactured into end products by vacuum freeze-drying. Dry-heating inactivation is a feasible way of terminal inactivation.

An existing terminal dry-heating inactivation method, where a vacuum freeze-drying product is inactivated by dry-heating under vacuum conditions, has good inactivation effect on lipid enveloped viruses such as HBV but poor inactivation effect on highly heat resistant lipid enveloped viruses, particularly on parvoviruses. For example, the researches of Roberts, et al. indicated that different non-lipid enveloped viruses had different heat resistance under the same treatment conditions: only 2.2 log of PPVs may be inactivated when treated by dry-heating at 80° C. even for 72 h. The report of Kim, et al, indicated that, the titer of PPVs (Porcine Parvoviuses) was merely reduced by 1.90 log by treating FVIII concentrate in a water bath at 100° C. for 30 min. Xiang Qingqun, et al., *Effects of Final Dry-heating on Non-enveloped Viruses in Coagulation Factor Concentrate*, Foreign Medical Sciences, Section of Bilogics for Prophylaxis, Diagnosis and Therapy, 1995, No. 06, pointed out that, after added into SD-inactivated high-purity FVIII and then freeze-dried, CPVs (Human Parvoviuses) were vacuum dry-heated upon the residual moisture of less than 2%, and only 2.1 log of CPVs was inactivated when treated at 80° C. for 72 hrs or at 90° C. for 10 hrs.

SUMMARY OF THE PRESENT INVENTION

To solve the above problems, the present invention provides a new method for terminal inactivation of pathogenic microorganisms.

The present invention provides a method for terminal inactivation of pathogenic microorganisms, comprising the following steps of:

a. vacuum freeze-drying a bio-product packaged in a container, feeding in a gas and sealing to obtain the end product; and b. performing inactivation by dry-heating.

Bio-products are products produced by conventional technologies or modern biotechnologies from microorganisms, cells, animal or human tissues and body fluids, etc., as raw materials for prophylaxis, therapy and diagnosis of human diseases, for example, blood products.

The dry-heating inactivation is a method of heating freeze-dried preparations and inactivating pathogenic microorganisms by dry-heating.

The gas in step a is an inert gas or a non-inert gas.

The inert gas is helium, neon, argon, krypton, xenon or radon; and, the non-inert gas is nitrogen, NO, $NO_2$, CO, $CO_2$, water vapor, air, deoxidized air, dehydrogenated air, deoxidized and dehydrogenated air, oxygen, hydrogen, $O_3$, methane, acetylene, ethanol, methyl ether, propane or butane.

The nitrogen is 99.999% nitrogen.

In step a, the amount of the gas fed is 0.4-1 atm by pressure in the container. Preferably, the amount of the gas fed is 0.4-0.9 atm by pressure in the container. Further preferably, the amount of the gas fed is 0.65-0.85 atm by pressure in the container.

In step b, the temperature for the inactivation by dry-heating is 0-130° C., and the treatment time is 0-200 hrs.

When the temperature is 60-110° C., the treatment time is 30 min-150 hrs.

Preferably, when the temperature is 80° C., the treatment time is 18-140 hrs; and, when the temperature is 100° C., the treatment time is 30-120 min.

Further preferably, when the temperature is 80° C., the treatment time is 36-72 hrs; and, when the temperature is 100° C., the treatment time is 60-90 min.

The method for terminal inactivation of pathogenic microorganisms provided by the present invention may effectively inactivate non-lipid enveloped viruses, with very excellent inactivation effects particularly to parvoviruses, being 10-1000 times of the existing activation method in efficiency, and may significantly improve the safety of bio-products; furthermore, this method has short treatment time, shortens the time for high-temperature virus inactivation by 10%-50% and greatly reduces the production cost, and thus has good industrial application prospects.

Apparently, according to the above contents of the present invention, modifications, replacements or alterations in many other forms may be made by general technical knowledge and common means in the art without departing from the basic technical concepts of the present invention mentioned above.

The above contents of the present invention will be further described as below in details by specific implementation ways in form of embodiments. However, the following instances should not be regarded as limitations to the scope of the above subject of the present invention. All techniques realized based on the above contents of the present invention shall fall into the scope of the present invention.

DETAILED DESCRIPTION OF THE PRESENT INVENTION

Experimental Materials

Figure 1:
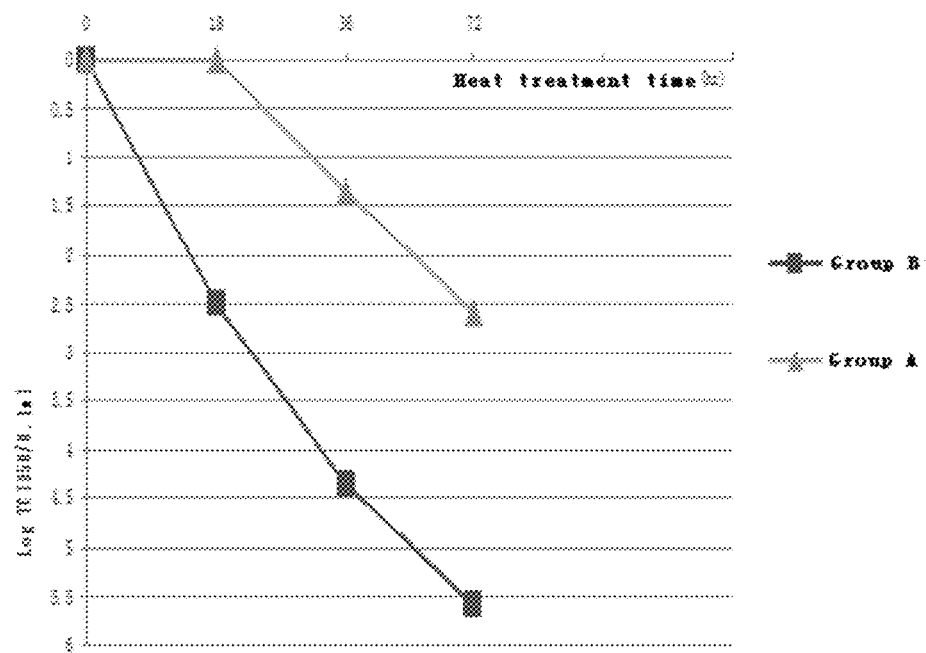
FIG. 1 shows a kinetic curve where PPVs are inactivated at 80° C. by dry-heating (in a drying oven)

Material 1:

PPVs: strain AV30, provided Chinese Veterinary Microorganism Culture Collection Center and stored in a basic titer of 10.0 Log $TCID_{50}$/ml at −70° C. Cell for cultivation: cell F81 (Cell Bank, Chinese Academy of Sciences). Titration of PPVs: 0.50 $TCID_{50}$/0.1 ml is detected by 96-well CPE and the titer is calculated on the basis of that result by the Karber method. The basic titer $\geq 10^6$.

Material 2:

Materials in formulations of common reagents or buffers: 0-25 mmol/l of sodium citrate; 10-150 mmol/l of NaCl; 1-10% of amino acid, which is glycine, histidine, lysine or salts thereof, or arginine or salts thereof; 1-5 mmol/l of soluble calcium salts; and, 0.5%-5% of albumin (BSA).

The following bio-products or materials are prepared with reference to methods recorded or cited in Liu Junxiang. *Blood Transfusion and Blood Products*. People's Medical Publishing House, 1996:

Material 3:

Intermediate of human coagulation factor VIII, prepared according to "Improved Glycine Precipitation" in the report of the blood separation center of Armand Frappier in Canada, with albumin and/or amino acid acting as the stabilizer.

Material 4:

Intermediate of human coagulation factor VIII, prepared according to "Heparin-Acid Precipitation" proposed by the plasma-protein separation laboratory and Elstree blood product laboratory in the Chuchill hospital, Oxford, UK, with albumin and/or amino acid acting as the stabilizer.

Material 5:

Intermediate of human coagulation factor VIII, prepared according to "Methods for Preparing High-purity VIII Concentrate from EAE-Fractgel TSK650M" proposed in the report of Burnouf, et al., from France, with albumin and/or amino acid acting as the stabilizer.

Material 6:

Intermediate of human coagulation factor VIII, prepared by dissolving cryoprecipitates with aqueous solution containing 3-10 IU/ml heparin sodium, PEG precipitating, centrifugally filtrating, S/D inactivating, column absorbing by DEAE-Sepharose Fast Flow or DEAE 650M, washing, eluting, ultrafiltering and concentrating, with albumin and/or amino acid acting as the stabilizer.

Material 7:

Intermediate of human fibrinogen (Fg), prepared by the Blomback method by fully dissolving cryoprecipitates, absorbing with $Al(OH)_3$ gel, filtering, inactivating lipid enveloped viruses by S/D, precipitating with PEG or glycine, ultrafiltering and purifying to form stock solution of human fibrinogen (Fg), with albumin and/or amino acid acting as the stabilizer to prepare human fibrinogen (Fg) (purity$\geq$90%, and concentration of protein $\geq$40 mg/ml).

Material 8:

Intermediate of human fibrinogen (Fg), prepared according to methods (Chon's low-temperature ethanol method, for short) recorded in *Preparation and Properties of Serum and Plasma Protein* released by E. J Chon: fully dissolving Fl precipitates obtained by Chon's low-temperature ethanol process, absorbing with $Al(OH)_3$ gel, filtering, inactivating lipid enveloped viruses by S/D, precipitating again with low-temperature ethanol, ultrafiltering and purifying to form the stock solution of human fibrinogen (Fg), with amino acid and/or albumin acting as the stabilizer to prepare the intermediate of human fibrinogen (purity$\geq$90%, and concentration of protein $\geq$40 mg/ml).

Material 9:

Intermediate of human prothrombin complex concentrate (PCC), prepared by absorbing the cold supernatant with DEAE-SephadexA50 gel, washing, eluting, filtering, inactivating lipid enveloped viruses by S/D, absorbing again by DEAE-Sepharose Fast Flow column gel (DEAE-Sepharose Fast Flow), washing, eluting, ultrafiltering and purifying to form the stock solution of human prothrombin complex concentrate (PCC), with amino acid and/or albumin acting as the stabilizer to prepare the intermediate of human prothrombin complex concentrate (specific activity $\geq$0.5 IU/ml, and concentration of protein $\approx$30 mg/ml).

Material 10:

Intermediate of human prothrombin complex concentrate (PCC), prepared by absorbing the cold supernatant with DEAE-SephadexA50 gel, washing, eluting, filtering, inactivating lipid enveloped viruses by S/D, absorbing again by DEAE-SephadexA50 gel, washing, eluting, ultrafiltering and purifying to form the stock solution of human prothrombin complex concentrate (PCC), with amino acid and/or albumin acting as the stabilizer to prepare the intermediate of human prothrombin complex concentrate (specific activity $\geq$0.5 IU/ml, and concentration of protein $\approx$30 mg/ml).

The above bio-products or materials should be stored at an ultra-low temperature of −70° C. if not used immediately.

Embodiment 1 Method for Inactivating Pathogenic Microorganisms Provided by the Invention 1. Treatment Method (1) The bottled material 3 is vacuum freeze-dried, under vacuum of 0.05 mbar, punctured through the rubber plug and fed with high-purity nitrogen (99.999%) to balance the pressure to 1 atm, and finally plugged for sealing, where the content of moisture is measured to be ≤2%.

(2) The bottled material 3 is dry-heated (in a drying oven) at 25° C. for 200 hrs.

Embodiment 2 Method for Inactivating Pathogenic Microorganisms Provided by the Invention 1. Treatment Method (1) The bottled material 4 is vacuum freeze-dried, under vacuum of 0.05 mbar, punctured through the rubber plug and fed with water vapor to balance the pressure to 0.4 atm, and finally plugged for sealing, where the content of moisture is measured to be ≤2%.

(2) The bottled material 4 is dry-heated (in a drying oven) at 130° C. for 1 min.

Embodiment 3 Method for Inactivating Pathogenic Microorganisms Provided by the Invention 1. Treatment Method (1) The bottled material 4 is vacuum freeze-dried, under vacuum of 0.05 mbar, punctured through the rubber plug and fed with high-purity nitrogen (99.999%) to balance the pressure to 0.9 atm, and finally plugged for sealing, where the content of moisture is measured to be ≤2%.

(2) The bottled material 4 is dry-heated (in a drying oven) at 60° C. for 150 hrs.

Embodiment 4 Method for Inactivating Pathogenic Microorganisms Provided by the Invention 1. Treatment Method (1) The bottled material 4 is vacuum freeze-dried, under vacuum of 0.05 mbar, punctured through the rubber plug and fed with hydrogen to balance the pressure to 0.65 atm, and finally plugged for sealing, where the content of moisture is measured to be ≤2%.

(2) The bottled material 4 is dry-heated (in a drying oven) at 110° C. for 30 min.

Embodiment 5 Method for Inactivating Pathogenic Microorganisms Provided by the Invention 1. Treatment Method (1) The bottled material 4 is vacuum freeze-dried, under vacuum of 0.05 mbar, punctured through the rubber plug and fed with $CO_2$ to balance the pressure to 0.851 atm, and finally plugged for sealing, where the content of moisture is measured to be ≤2%.

(2) The bottled material 4 is dry-heated n a drying oven) at 60° C. for 150 min.

Embodiment 6 Method for Inactivating Pathogenic Microorganisms Provided by the Invention 1. Treatment Method (1) The material 4 (the intermediate of human coagulation factor VIII) is vacuum freeze-dried, under vacuum of 0.05 mbar, fed in situ with hydrogen to balance the pressure to 1 atm, and finally plugged for sealing, where the content of moisture is measured to be ≤2%.

(2) The material 4 is dry-heated (in a drying oven) at 110° C. for 120 min.

Embodiment 7 Method for Inactivating Pathogenic Microorganisms Provided by the Invention 1. Treatment Method (1) The bottled material 5 is vacuum freeze-dried, under vacuum of 0.05 mbar, punctured through the rubber plug and fed with argon to balance the pressure to 0.4 atm, and finally plugged for sealing, where the content of moisture is measured to be ≤2%.

(2) The bottled material 5 is dry-heated (in a drying oven) at 80° C. for 36 hrs.

Embodiment 8 Method for Inactivating Pathogenic Microorganisms Provided by the Invention 1. Treatment Method (1) The bottled material 6 is vacuum freeze-dried, under vacuum of 0.05 mbar, directly fed in situ with high-purity nitrogen (99.999%) via an aseptic conduit to balance the pressure to 0.65 atm, and finally plugged for sealing, where the content of moisture is measured to be ≤2%.

(2) The bottled material 6 is dry-heated (in a drying oven) at 80° C. for 48 hrs.

Embodiment 9 Method for Inactivating Pathogenic Microorganisms Provided by the Invention 1. Treatment Method (1) The bottled material 4 is vacuum freeze-dried, under vacuum of 0.05 mbar, directly fed in situ with high-purity nitrogen (99.999%) via an aseptic conduit to balance the pressure to 0.9 atm, and finally plugged for sealing, where the content of moisture is measured to be ≤2%.

(2) The bottled material 4 is dry-heated (in a drying oven) at 80° C. for 72 hrs.

Embodiment 10 Method for Inactivating Pathogenic Microorganisms Provided by the Invention 1. Treatment Method (1) The bottled material 7 is vacuum freeze-dried, under vacuum of 0.05 mbar, punctured through the rubber plug and fed with high-purity nitrogen to balance the pressure to 0.85 atm, plugged for sealing and capped, where the content of moisture is measured to be ≤2%.

(2) The bottled material 7 is dry-heated (in a water bath) at 100° C. for 120 min.

Embodiment 11 Method for Inactivating Pathogenic Microorganisms Provided by the Invention 1. Treatment Method (1) The bottled material 8 is vacuum freeze-dried, under vacuum of 0.05 mbar, directly fed in situ with acetylene via an aseptic conduit to balance the pressure to 1 atm, plugged for sealing and capped, where the content of moisture is measured to be ≤2%.

(2) The bottled material 8 is dry-heated (in a water bath) at 100° C. for 120 min.

Embodiment 12 Method for Inactivating Pathogenic Microorganisms Provided by the Invention 1. Treatment Method (1) The bottled material 8 is vacuum freeze-dried, under vacuum of 0.05 mbar, directly fed in situ with compressed air via an aseptic conduit to balance the pressure to 0.85 atm, plugged for sealing and capped, where the content of moisture is measured to be ≤2%.

(2) The bottled material 8 is dry-heated (in a water bath) at 100° C. 120 min.

Embodiment 13 Method for Inactivating Pathogenic Microorganisms Provided by the Invention 1. Treatment Method (1) The bottled material 9 is vacuum freeze-dried, under vacuum of 0.05 mbar, directly fed in situ with compressed air via an aseptic conduit to balance the pressure to 0.65 atm, plugged for sealing and capped, where the content of moisture is measured to be ≤2%.

(2) The bottled material 8 is dry-heated (in a water bath) at 100° C. for 120 min.

Embodiment 14 Method for Inactivating Pathogenic Microorganisms Provided by the Invention 1. Treatment Method (1) The bottled material 4 is vacuum freeze-dried, under vacuum of 0.05 mbar, punctured through the rubber plug and fed with $NO_2$ to balance the pressure to 0.9 atm, plugged for sealing and capped, where the content of moisture is measured to be ≤2%.

(2) The bottled material 4 is dry-heated n a drying oven) at 100° C. for 60 min.

Embodiment 15 Method for Inactivating Pathogenic Microorganisms Provided by the Invention 1. Treatment Method (1) The bottled material 4 is vacuum freeze-dried, under vacuum of 0.05 mbar, punctured through the rubber plug and fed with high-purity nitrogen (99.999%) to balance the pressure to 1 atm, and finally plugged for sealing, where the content of moisture is measured to be ≤2%.

(2) The bottled material 4 is dry-heated (in a water bath) at 100° C. for 90 min.

The beneficial effects of the present invention will be described as below by embodiments.

Embodiment 1 Method for Inactivating Pathogenic Microorganisms Provided by the Invention 1. Treatment Method (1) Porcine parvoviruses (PPV) as the virus model are uniformly mixed with the material 9, i.e., intermediate of PCC, by an inoculation amount of 10% (w/w), and then vacuum freeze-dried; and, the freeze-dried samples are divided into groups A and B, where the group A is one in vacuum, while the group B is one treated according to the method provided by the present invention.

Group A: the sample is plugged for sealing in a cabinet under vacuum of 0.05 mbar and capped, where the content of moisture in the sample is measured to be ≤2%;

Group B: under vacuum of 0.05 mbar, the bottled material is punctured through the rubber plug and fed with high-purity nitrogen until the pressure in the bottle detected by a miniature electronic pressure gauge is 1 atm, plugged for sealing and capped, where the content of moisture is measured to be ≤2%.

(2) Sampling during dry-heating at 100° C. is performed at 10 min, 30 min, 60 min and 90 min, respectively; the samples are cooled and kept at −70° C. for measurement of the titer of the PPVs; and, by calculation, the reduced value of titer of viruses=titer before heating-titer after heating, unit: log $TCID_{50}/0.1$ ml.

2. Results of Treatment

Table 1 shows results of PPV titer detection of the treated PPC.

TABLE 1

| | Reduced Values at PPV Titer | | | |
| --- | --- | --- | --- | --- |
| Test groups | Reduced values of titer of PPVs Ntv h e n dry-heated (in a water bath) at 100° C. at different time ($TCID_{50}/0.1$ ml) | | | |
| | 0 min | 30 min | 60 min | 90 min |
| A | 0 | 2.5 | 3.58 | 5.42 |
| B | 0 | 3.42 | 4.34 | 6.50 |
| $Log^{-1}$ (B-A) | 0 | 10 | 10 | 10 |

Log $TCID_{50}/0.1$ ml Minimum virus detection limit in this experiment: ≤0.50 Log $TCID_{50}/0.1$ ml.

As shown in Table 1, at different treatment time points, the reduced value of titer of parvoviruses in the sample, treated according to the method provided by the present invention (group B), is more than 10 times of that according to the existing method (group A); the reduced value of tilter of viruses after 30 min of treatment according to the method provided by the present invention (group B) is equivalent to that after 60 min of treatment according to the existing method (group A). Therefore, it is indicated that the time required by the method provided by the present invention to achieve the same inactivation effects is far shorter than that required by the existing method.

The results of tests show that the method provided by the present invention can inactivate parvoviruses more effectively and has short inactivation time.

Embodiment 2 Method for Inactivating Pathogenic Microorganisms Provided by the Invention 1. Treatment Method (1) Porcine parvoviruses (PPV) as the virus model are uniformly mixed with the material 4, i.e., intermediate of human coagulation factor VIII, by an inoculation amount of 10% (w/w), and then vacuum freeze-dried; and, the freeze-dried samples are divided into groups A and B, where the group A is one in vacuum, while the group B is one treated according to the method provided by the present invention.

Group A: the sample is plugged for sealing in a cabinet under vacuum of 0.05 mbar and capped, where the content of moisture in the sample is measured to be ≤2%;

Group B: under vacuum of 0.05 mbar, the bottled material is punctured through the rubber plug and fed with high-purity nitrogen until the pressure in the bottle detected by a miniature electronic pressure gauge is 0.85 atm, plugged for sealing and capped, where the content of moisture is measured to be ≤2%.

(2) Sampling during dry-heating (in a drying oven) at 80° C. is performed at 0 hr, 18 hrs, 36 hrs and 72 hrs, respectively; the samples are cooled and kept at −70° C. for measurement of the titer of the PPVs; and, by calculation, the reduced value of titer of viruses=titer before heating-titer after heating, unit: log $TCID_{50}$/0.1 ml.

2. Results of Treatment

Table 1 and FIG. 1 show reduced values of titer of PPVs.

TABLE 2

Reduced Values of titer of PPVs when dry-heated (in a drying oven) at 80° C. at different time

| Test groups | Reduced values of titer of PPVs when dry-heated (in a drying oven) at 80° C. at different time ($TCID_{50}$/0.1 ml) | | | |
|---|---|---|---|---|
| | 0 hr | 18 hrs | 36 hrs | 72 hrs |
| A | 0 | 6 | 1.34 | 2.58 |
| B | 0 | 2.50 | 4.34 | 5.58 |
| $Log^{-1}$ (B-A) | / | 316.23 | 1000.00 | 1000.00 |

Log $TCID_{50}$/0.1 ml Minimum virus detection limit in this experiment: ≤0.50 Log $TCID_{50}$/0.1 ml.

As shown in Table 2 and FIG. 1, at different treatment time points, the reduced value of titer of parvoviruses in the sample, treated according to the method provided by the present invention (group B), is 316-1000 times of that according to the existing method (group A); the reduced value of tilter of viruses after 18 hrs of treatment according to the method provided by the present invention (group B) is equivalent to that after 72 hrs of treatment according to the existing method (group A). Therefore, it is indicated that the time required by the method provided by the present invention to achieve the same inactivation effects is ¼ of the time required by the existing method.

The results of tests show that the method provided by the present invention can inactivate parvoviruses more effectively and has short inactivation time.

Embodiment 3 Method for Inactivating Pathogenic Microorganisms Provided by the Invention 1. Treatment Method (1) Porcine parvoviruses (PPV) as the virus model are uniformly mixed with the material 4, i.e., intermediate of human coagulation factor VIII, by an inoculation amount of 10% (w/w), and then vacuum freeze-dried; and, the freeze-dried samples are divided into groups A and B, where the group A is one in vacuum, while the group B is one treated according to the method provided by the present invention.

Group A: the sample is plugged for sealing in a cabinet under vacuum of 0.05 mbar and capped, where the content of moisture in the sample is measured to be ≤2%;

Group B: under vacuum of 0.05 mbar, the bottled material is punctured through the rubber plug and fed with high-purity nitrogen until the pressure in the bottle detected by a miniature electronic pressure gauge is 0.4 atm, plugged for sealing and capped, where the content of moisture is measured to be ≤2%.

(2) Sampling during dry-heating (in a water bath) at 100° C. is performed at 10 min, 30 min, 60 min and 90 min, respectively; the samples are cooled and kept at −70° C. for measurement of the titer of the PPVs; and, by calculation, the reduced value of titer of viruses=titer before heating-titer after heating, unit log $TCID_{50}$/0.1 ml.

2. Results of Treatment

Figure 2:
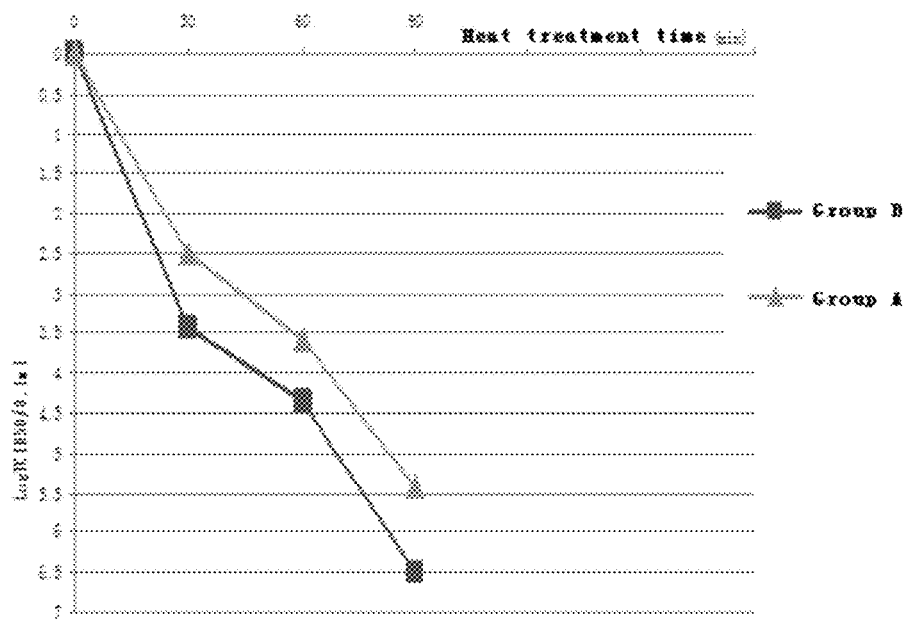
FIG. 2 shows a kinetic curve where PPVs are inactivated at 100° C. by dry-heating (in a water bath).

Table 3 and FIG. 2 show reduced values of titer of PPVs.

TABLE 3

Reduced values of titer of PPVs when dry-heated (in a water bath) at 80° C. at different time

| Test groups | Reduced values of titer of PPVs when dry-heated (in a water bath) at 80° C. at different time ($TCID_{50}$/0.1 ml) | | | |
|---|---|---|---|---|
| | 0 min | 30 min | 60 min | 90 min |
| A | 0 | 0.38 | 2.17 | 4.08 |
| B | 0 | 3.73 | 4.51 | 6.59 |
| $Log^{-1}$ (B-A) | 0 | 2238.72 | 218.78 | 323.59 |

Log $TCID_{50}$/0.1 ml Minimum virus detection limit in this experiment: ≤0.50 Log $TCID_{50}$/0.1 ml.

As shown in Table 3 and FIG. 2, at different treatment time points, the reduced value of titer of parvoviruses in the sample, treated according to the method provided by the present invention (group B), is 218-2238 times of that according to the existing method (group A); the reduced value of tilter of viruses after 60 min of treatment according to the method provided by the present invention (group B) is higher than that after 90 min of treatment according to the existing method (group A). Therefore, it is indicated that the time required by the method provided by the present invention to achieve the same inactivation effects is significantly shorter than the time required by the existing method.

The results of tests show that the method provided by the present invention can inactivate parvoviruses more effectively and has short inactivation time.

In conclusion, terminal inactivation of pathogenic microorganisms provided by the present invention may effectively inactivate non-lipid enveloped viruses, such as parvoviruses, and improve the safety of bio-products; furthermore, it has short activation time, low production cost and good application prospects.

We claim:

1. A method for terminal inactivation of parvovirus, comprising the following steps:
   a. vacuum freeze-drying a bio-product packaged in a container, feeding in a gas and sealing; and
   b. performing inactivation by dry-heating in the container to obtain an end product;
   wherein the gas is nitrogen; and the purity of the nitrogen is 99.999%;
   in step a, the amount of the gas fed is 0.4-1 atm by pressure in the container;
   in step b, a temperature for the inactivation by dry-heating is 0-130° C., and a treatment time is 0-200 hrs; and when the temperature is 60-110° C., the treatment time is 30 min-150 hrs.

2. The method according to claim 1, wherein the amount of the gas fed is 0.4-0.9 atm by pressure in the container.

3. The method according to claim 2, wherein the amount of the gas fed is 0.65-0.85 atm by pressure in the container.

4. The method according to claim 1, wherein when the temperature is 80° C., the treatment time is 18-140 hrs.

5. The method according to claim 4, wherein when the temperature is 80° C., the treatment time is 36-72 hrs.

6. The method according to claim 1, wherein when the temperature is 100° C., the treatment time is 30-120 min.

7. The method according to claim 6, wherein when the temperature is 100° C., the treatment time is 60-90 min.

* * * * *